(12) United States Patent
Urie

(10) Patent No.: US 9,352,132 B2
(45) Date of Patent: May 31, 2016

(54) CATHETER GUIDE WIRE

(71) Applicant: MEDIPLUS LIMITED, Buckinghamshire (GB)

(72) Inventor: Robert Graham Urie, Buckinghamshire (GB)

(73) Assignee: Mediplus Limited, Buckinghamshire (GB)

( * ) Notice: Subject to any disclaimer, the term of this patent is extended or adjusted under 35 U.S.C. 154(b) by 241 days.

(21) Appl. No.: 14/287,336

(22) Filed: May 27, 2014

(65) Prior Publication Data

US 2014/0350519 A1  Nov. 27, 2014

Related U.S. Application Data

(63) Continuation of application No. 10/597,893, filed as application No. PCT/GB2005/000494 on Feb. 11, 2005, now abandoned.

(30) Foreign Application Priority Data

Feb. 11, 2004 (GB) .................................. 0402930.2

(51) Int. Cl.
*A61M 25/09* (2006.01)
*A61M 25/00* (2006.01)
*A61M 25/06* (2006.01)
*A61M 25/01* (2006.01)

(52) U.S. Cl.
CPC ..... *A61M 25/09041* (2013.01); *A61M 25/0017* (2013.01); *A61M 25/0606* (2013.01); *A61M 25/09* (2013.01); *A61M 2025/0188* (2013.01); *A61M 2025/0915* (2013.01); *A61M 2025/09083* (2013.01)

(58) Field of Classification Search
CPC ..................... A61M 25/0017; A61M 25/0606; A61M 25/09; A61M 25/09041
USPC ........................................................ 600/585
See application file for complete search history.

(56) References Cited

U.S. PATENT DOCUMENTS

| 4,619,644 A | 10/1986 | Scott |
| 6,685,671 B1 | 2/2004 | Oishi et al. |
| 2002/0077686 A1 | 6/2002 | Westlund et al. |
| 2002/0147491 A1 | 10/2002 | Khan et al. |
| 2002/0156397 A1 | 10/2002 | Cornish et al. |
| 2004/0059259 A1 | 3/2004 | Cornish et al. |

FOREIGN PATENT DOCUMENTS

| EP | 1378262 A2 | 1/2004 |
| WO | 99/64100 A1 | 12/1999 |

*Primary Examiner* — Lee S Cohen
*Assistant Examiner* — Emily Lloyd
(74) *Attorney, Agent, or Firm* — Renner, Otto, Boisselle & Sklar, LLP

(57) ABSTRACT

A catheter guidewire for facilitating introduction of a flexible catheter into the human body (e.g., into the bladder) has a proximal end having a first stiffness which is sufficient to facilitate guidance of a stiff plastic expansion sheath through the tissue. A distal end of the guide wire has a second stiffness, substantially less than the first stiffness, to avoid damage to internal walls of the bladder. Preferably, the guide wire incorporates an intermediate portion having a stiffness between the first stiffness value and the second stiffness value.

18 Claims, 3 Drawing Sheets

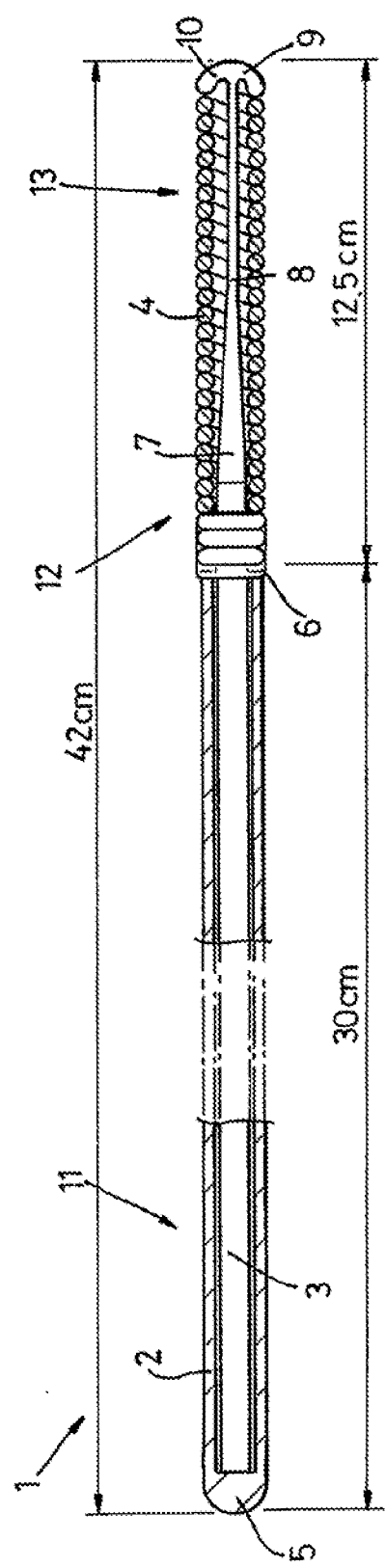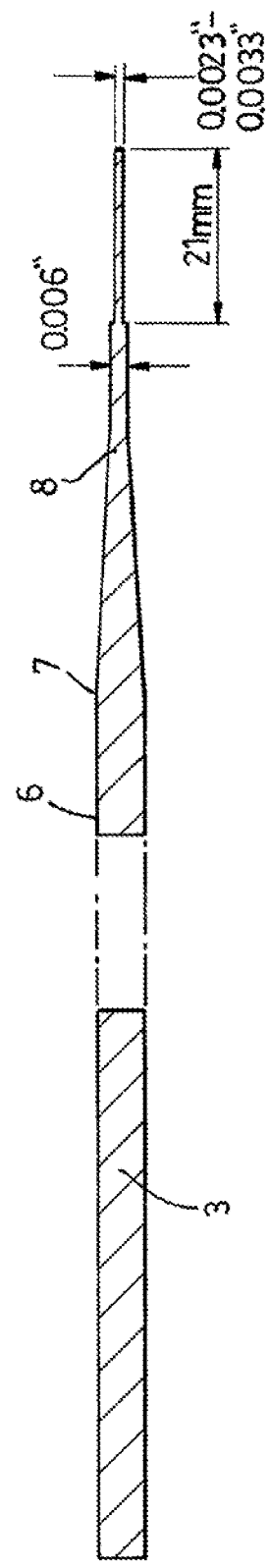
*Fig. 1*
*Fig. 2*

CATHETER GUIDE WIRE

RELATED APPLICATION DATA

This application is a continuation of U.S. patent application Ser. No. 10/597,893 filed May 20, 2008, now abandoned, which is a national phase of International Application No. PCT/GB2005/000494, filed Feb. 11, 2005, all of which are incorporated herein by reference.

BACKGROUND

The present invention relates to guide wires for the insertion of catheters into the human or animal body and in particular, though not exclusively, to guide wires suitable for the insertion of the catheter into the bladder.

Insertion of a flexible catheter into the human bladder via the supra-pubic region can present particular problems. In one conventional technique, a large bore needle having an internal diameter capable of receiving the flexible catheter is used to penetrate the skin, underlying tissue and bladder. A flexible catheter is then introduced into the needle and inserted into the bladder, following which the needle may be withdrawn. This requires the use of a needle having large diameter sufficient to accommodate a catheter and of sufficient strength to penetrate the relative tough supra-pubic tissue area. This requires the use of a needle having an outside diameter that is significantly larger than the outside diameter of the flexible catheter (which itself is typically approximately 4 or 5 mm), thereby forming a hole in the tissue significantly larger than strictly necessary. Great care has to be exercised by the clinician introducing the needle to avoid over- or under-penetration of the needle.

In another conventional technique, a trocar having a stiff penetrative tip (e.g. of medical grade stainless steel) and a stiff outer plastic sheath is inserted into the bladder through the supra-pubic region. The trocar is then withdrawn through the sheath, leaving the sheath in situ, penetrating the bladder through the supra-pubic region. A flexible catheter is then introduced into the bladder through the sheath. The plastic sheath is of the peelable variety, so that once the flexible catheter is introduced into the bladder, the sheath can be split along its entire length, stripped away from the flexible catheter and removed from the body. This leaves the flexible catheter in situ. A potential drawback with this technique is that the initial penetration of the supra-pubic region is, like the previously described technique, performed with a penetrative instrument having an outside diameter of similar dimensions to the flexible catheter that is eventually introduced (e.g. of the order of 5 mm or so). Therefore, again, the clinician must exercise great care to avoid over-penetration of the bladder and potential damage to the opposite bladder wall.

SUMMARY

The present invention seeks to provide an improved method and apparatus for insertion of a flexible catheter into a human or animal body. In one aspect, the invention seeks to provide a guidewire technique to overcome some or all of the disadvantages associated with the prior art.

According to one aspect, the present invention provides a guidewire for introduction into a body via a hollow needle, comprising:

a proximal end having a stiffness greater than 10 N; and
a distal end having a stiffness less than 3 N, the stiffness being defined as the force required to produce an angular lateral displacement of 30 degrees when applied at a distance of 10 mm along the respective length of guidewire.

According to another aspect, the present invention provides a guidewire for introduction into a body via a hollow needle, comprising:

a proximal end having a first stiffness;
a distal end having a second stiffness less than said first stiffness; and
an intermediate portion having a stiffness lying between the first and second stiffness values.

According to another aspect, the present invention provides a method for introducing a catheter into the bladder of the human body in the supra-public region comprising the steps of:

introducing a needle into the bladder via the supra-pubic region, the needle having an outside diameter less than 2 mm;
inserting a guidewire having an outside diameter less than 2 mm into the bladder through an internal bore of the needle;
withdrawing the needle over the guidewire;
introducing a peelable catheter sheath into the bladder over the guidewire, the catheter sheath having a distal end of outside diameter less than approximately 2 mm and a proximal end having an outside diameter of at least 4 mm;
withdrawing the guidewire through the catheter sheath;
inserting a flexible catheter into the bladder through the catheter sheath; and
peeling away the catheter sheath from the flexible catheter leaving the flexible catheter in situ.

According to another aspect, the present invention provides a bladder drainage kit comprising:

a guidewire having an outside diameter less than 2 mm and having a proximal end having a first stiffness and a distal end having a second stiffness, the second stiffness being less than the first stiffness;

a peelable catheter sheath adapted to receive the guidewire and to penetrate the supra-pubic region of the human body using the proximal portion of the guidewire as a guide, the catheter sheath having an inside diameter at its distal end approximately equal to the outside diameter of the guidewire, and an inside diameter at its proximal end of at least 4 mm for receiving a flexible drainage catheter.

BRIEF DESCRIPTION OF THE DRAWINGS

Embodiments of the present invention will now be described by way of example and with reference to the accompanying drawings in which:

FIG. 1 shows an axial cross-section of a guidewire according to a preferred embodiment of the present invention;

FIG. 2 shows an axial cross-section of a center wire of the guidewire of FIG. 1;

DETAILED DESCRIPTION

Figure 3:
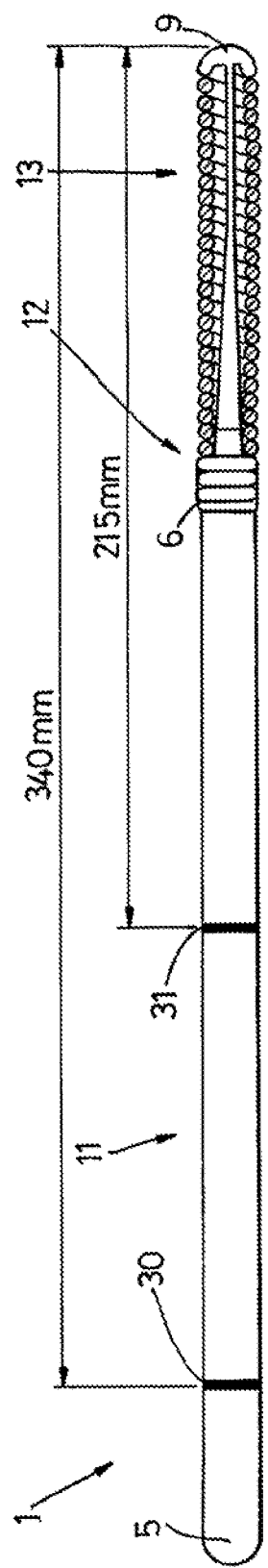
FIG. 3 shows a side view of the complete guidewire of FIG. 1.

A feature of the method of the present invention is that a guide wire can be used to significantly reduce the diameter of needle or trocar required to penetrate the bladder. This is particularly significant in the supra-pubic region where the tissue is particularly tough. In the preferred technique, a small diameter needle (e.g. of the order of 1 mm outside diameter) is inserted into the bladder in the supra-pubic region. The relatively small diameter needle is much easier to control during penetration of the tissue.

A thin guidewire is then introduced into the bladder via tie needle, such that it extends into the bladder. The needle is then withdrawn over the guidewire, leaving the guidewire in place. A stiff plastic sheath having a distal end which tapers down to a diameter similar to that of the guidewire is introduced into the bladder through the skin and tissue using the guidewire as a guide. This expands the existing hole in the tissue. A flexible catheter is then introduced into the plastic sheath and thereby into the bladder. The plastic sheath is of the peelable variety, so that once the flexible catheter is introduced into the bladder, the sheath can be split along its entire length, stripped away from the flexible catheter and removed from the body. This leaves the flexible catheter in situ. A significant advantage of this procedure is that the initial penetration of the supra-pubic region is by way of small diameter needle; the expansion of the initial hole can then be performed under the control of a guidewire.

In order to successfully perform this procedure, the guidewire must have a high degree of stiffness in order to facilitate and guide the penetration, into the body, of the relatively larger plastic sheath. Otherwise the pressure being applied on the plastic sheath to displace tough tissue will distort the guidewire. This high stiffness in turn again increases the likelihood of internal damage to the bladder caused by over-insertion of the guidewire, such that the distal end thereof collides with an opposite internal wall of the bladder. Therefore, the clinician must exercise great care not to over-insert the guidewire, despite significant variations in physique of different patients (e.g. the depth and stiffness or muscle tone of tissue to be penetrated).

With reference to FIG. 1 there is shown a guidewire 1 of a preferred embodiment. The guidewire comprises outer tubing 2, preferably formed from stainless steel, which is filled with a solid core 3, also preferably formed from stainless steel. The outer tubing 2 extends from a proximal end 5 of the guidewire 1 to a first intermediate position 6 where it is welded, brazed or otherwise fixed or bonded to a tightly would coil 4 of substantially the same outside diameter as the outer tubing 2. The coil 4 extends from the first intermediate position 6 to a distal end 9 of the guidewire 1.

The solid core 3 extends throughout the outer tubing 2 and extends beyond the first intermediate position to the distal end 9 of the guidewire. At the first intermediate position 6, or slightly beyond it at a second intermediate position 7 towards the distal end 9, the solid core 3 commences a taper. The taper ends at a third intermediate position 8. The solid core 8 terminates at the distal end in a 'mushroom' configuration where it is welded, brazed or otherwise fixed or bonded to the tightly wound coil 4.

As is particularly illustrated in FIG. 1, the guidewire 1 therefore provides three distinct portions. These are: a first ('proximal') portion 11 extending from the proximal end 5 to the first intermediate position 6; a second ('intermediate') portion 12 extending from the first intermediate position 6 to the third intermediate position 8; and a third ('distal') portion 13 extending from the third intermediate position 8 to the distal end 9.

The combination of the outer tubing 2, the coil 4 and the solid core 3 effectively provides a guidewire 1 having a first stiffness at the proximal end (and generally extending throughout the proximal portion 11 to the first intermediate position 6), a second stiffness at the distal end 9 (and generally extending throughout the distal portion 13 to the third intermediate position 8) in which the second stiffness value is significantly less than the first stiffness value. In the intermediate portion 12, the stiffness value lies between that of the first and second stiffness values and may generally vary over the length thereof.

In the following preferred values, the stiffness is defined as the force required to produce an angular lateral displacement of 30 degrees when applied at a distance of 10 mm along the respective length of guidewire. Preferably, the stiffness of the proximal portion 11 is in excess of 10 N, and more preferably lies within the range 15 to 20 N. Preferably, the stiffness of the distal portion 13 is less than 3 N, and more preferably lies within the range 0.2 to 1 N. Preferably, the stiffness of the intermediate portion 12 lies in the range between that of the adjacent proximal and distal portions, and preferably it has a gradual or stepped reduction in stiffness over the length of the intermediate portion 12. In preferred embodiments, the stiffness of the intermediate portion lies in the range 5 N to 8 N.

In the preferred arrangement as shown, the outer tubing has an outside diameter approximately 0.0355 inch or 0.0360 inch (900 or 915 microns). The outer tubing has a length of 30 cm. The coil has an outside diameter of approximately 0.0370 inch (940 microns) and a coiled length of approximately 12.5 cm. The solid core 3 has a maximum outside diameter (in the proximal portion) of approximately 0.020 inch (500 microns) and an overall length of approximately 42 cm. The solid core 3 has a diameter tapering to approximately 0.006 inch (150 microns) at the third intermediate position 8 and a length of distal portion of approximately 21 mm. The solid core 3 may taper in the distal portion 13 down to a diameter of between approximately 0.0023 inch and 0.0033 inch (58 to 84 microns).

In another arrangement, the outer tubing and coil have an outside diameter of approximately 750 microns. In a general aspect, the guidewire has an outside diameter of less than 2 mm and preferably less than or equal to 1 mm, e.g. in the range 750 to 1000 microns.

It will be understood that these dimensions may need to be varied in order to provide utility in different regions of the body and possibly for different patient morphology.

More generally, the guidewire 1 preferably has a distal end which extends over a length of between 10 and 15 cm, and more preferably over a length of 12.5 cm.+.1 cm. Preferably, the distal end comprises the distal portion 13 and the intermediate portion 12. In another general arrangement, the guidewire 1 has a distal portion that extends over a length of between 2 and 8 cm and an intermediate portion that extends over a length of between 2 and 8 cm. More preferably, the distal end extends over a length of at least 2 cm and the intermediate portion extends over a length of 4 cm±1 cm.

The materials used are preferably 304 stainless steel throughout although other clinical grade materials may be considered.

Preferably, the guidewire is provided with reference markings at predetermined positions along its length. With reference to FIG. 3, the guidewire 1 preferably includes a first reference mark 30 at a distance of 340 mm from the distal end 5 and a second reference mark 31 at a distance of 215 mm from the distal end. The function of the reference marks will become apparent from the description hereinafter.

Figure 4:
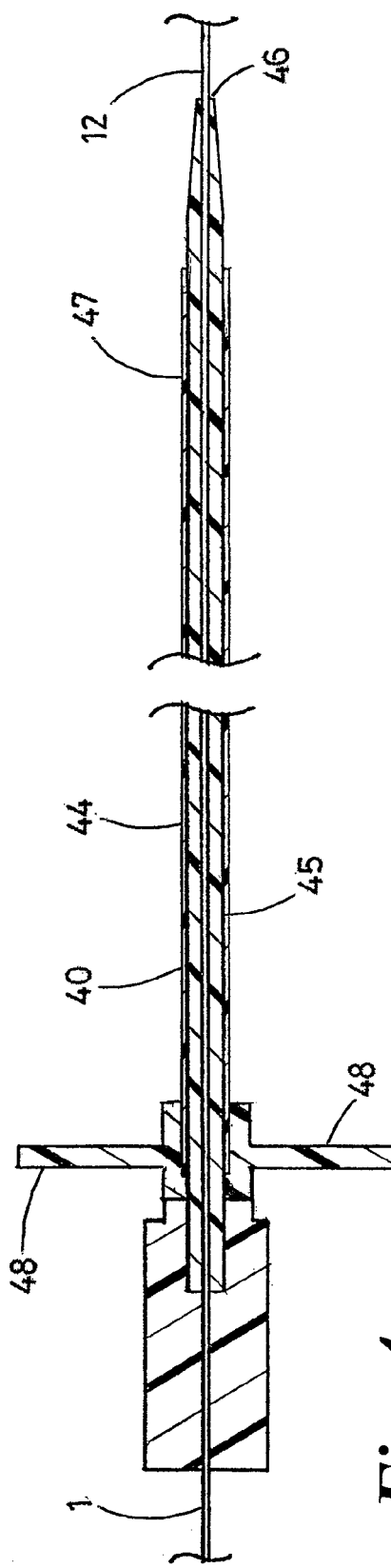
FIGS. 4-6 show a schematic diagram illustrating a needle, a plastic catheter sheath with peelable outer skin and catheter, useful in explaining a method of use of the guidewire of the present invention.
Figure 5:
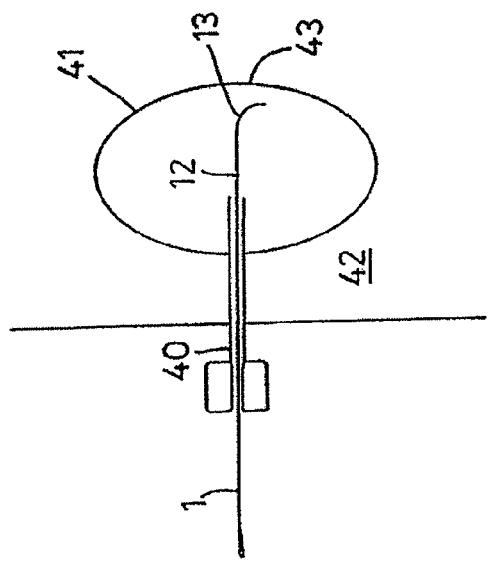
Figure 6:
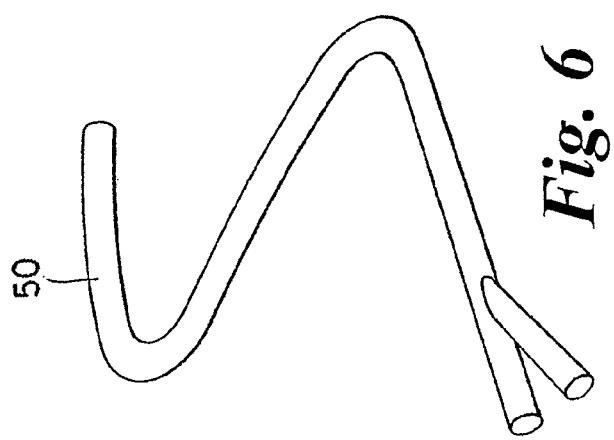

With reference to FIGS. 4-6, in a preferred arrangement, the guidewire is deployed in the following manner.

As seen in FIG. 5, a needle 40 of gauge 1 mm and length 7 mm is introduced into the bladder 41 through the supra-pubic tissue 42. The guidewire 1 is introduced into the bladder 41 through the needle. An important feature of the guidewire is that the distal portion 13 is relatively flexible with minimal stiffness (sufficient to allow convenient introduction into and through the needle) and is unable to cause damage to the internal walls of the bladder 41, especially at a location 43 opposite to the point of entry of the needle 40. Preferably, the intermediate portion 12 has a sufficient increase in stiffness over the distal portion 13 to provide tactile feedback to the clinician. In other words, when the guidewire has been passed into the bladder to an extent that the intermediate portion 12 reaches the opposite bladder wall 43, its collision with the wall will be evident to the clinician by simple change in resistance to further motion.

Despite the increased stiffness of the guidewire at that point, where the intermediate portion reaches the bladder wall 43, the existence of the more flexible (and now curved) distal portion 13 prevents damage to the bladder walls.

At this point, the clinician ceases further entry of the guidewire, and withdraws the needle 40 over the proximal end 11 of the guidewire 1 still outside the body. Following removal of the needle, a stiff plastic sheath, or preferably a pair of coaxial sheaths 44, 45, are slid over the guidewire 1 from its proximal end, preferably up to the point where the first or second reference mark appears (depending upon the type of sheath being used), as illustrated in FIG. 4. The stiff plastic sheaths 44 and 45 have a tapered end 46 adapted to form a snug sliding fit over the guidewire 1, i.e. having an inside diameter slightly larger than that of the outer tube 2 and coil 4.

The stiff plastic sheath provides a gradual increase in diameter increasing from approximately 1.2 mm outside diameter at its distal end 46 to 6 mm outside diameter for the main body portion 47. In the preferred embodiment, the outer sheath 44 of the coaxial pair of sheaths is formed from a relative thin and frangible plastics material and includes two lugs 48 at the proximal end. The inner sheath 45 is rather more robust and provides the mechanical strength required.

In use, the plastic sheaths are adapted to be guided by the guidewire into the tissue to expand the hole already formed by the needle. Particularly in the supra-pubic region, entry of the plastic sheath encounters significant resistance, increasing the dimension of hole in the tissue from the needle diameter (e.g. 1 mm to 6 mm). An important feature of the guidewire described herein is to provide a stiff proximal portion of the guidewire that is adequate to provide the guiding function, while providing a sufficiently flexible distal portion to avoid damage to internal walls of the bladder. It has been found that guidewires that are sufficiently flexible to avoid risk of damage to internal walls of the bladder are generally insufficiently stiff to provide adequate guidance to the plastic sheath insertion through certain tissue types in specific regions of the body, e.g. the supra-pubic region.

Once the plastic sheaths 44, 45 have been inserted, the guidewire 1 can be withdrawn. The inner sheath 45 can also be withdrawn. At that time, the desired bladder drainage catheter 50 (FIG. 6) formed from soft, flexible plastic tubing (e.g. of approximately 4 mm outside diameter) can be introduced into the bladder via the outer stiff plastic sheath 44. Once this action is completed, the stiff plastic sheath 44 can be removed by tearing along its length. In other words, the clinician may grasp the lugs 48 and strip or peel the plastic sheath 44 away; withdrawing the distal portion contained within the body while doing so.

In a general aspect, the plastic sheath 44 has a distal end of inside diameter approximately equal to the outside diameter of the guidewire, and a proximal end of inside diameter sufficient to receive the flexible catheter, e.g. at least 4 mm.

The use of a guidewire having at least two grades of stiffness, and preferably at least three, along its length, facilitates the provision of several important features. Firstly, the guidewire can be sufficiently stiff or rigid in the proximal portion to ensure adequate guidance of the sheath which expands the needle hole. At the same time, the flexible distal end protects the bladder internal walls from damage.

Secondly, the graduated stiffness in the intermediate portion provides the clinician with tactile feedback of the positioning of the guidewire within the bladder.

It will be understood that the stiffness of the various distal, intermediate and proximal portions need not be invariant along the length of the respective portion.

It will be understood that, throughout the present description, the dimensions of the various components of the preferred embodiments are illustrative only.

Other embodiments are intentionally within the scope of the accompanying claims.

What is claimed is:

1. A guidewire for introduction into the supra-pubic region of a human body via a hollow needle that penetrates skin, underlying tissue and a bladder in the human body, the guidewire comprising a proximal end portion, a distal end portion and an intermediate portion extending between the proximal and distal end portions, the distal end portion and intermediate portion including a central core and a coil surrounding the central core, the central core having a tapered portion coextending with the intermediate portion and a uniform diameter portion terminating at and joined to an end member located at a distal end of the coil, and wherein the proximal end portion has a first stiffness, the distal end portion has a second stiffness less than the first stiffness, and the intermediate portion has a stiffness lying between the first stiffness of the proximal end portion and the second stiffness of the distal end portion.

2. The guidewire of claim 1, wherein the intermediate portion tapers inwardly going from the proximal end portion to the distal end portion.

3. The guidewire of claim 1, wherein the distal end and intermediate portions have a collective length between 10 and 15 cm.

4. The guidewire of claim 3, wherein the distal end and intermediate portions have a collective length of 12.5 cm±1 cm.

5. The guidewire of claim 1, wherein distal end portion has a length between 2 and 8 cm, and the intermediate portion has a length between 2 and 8 cm.

6. The guidewire of claim 1, wherein distal end portion has a length of at least 2 cm and the intermediate portion has a length of 4 cm±1 cm.

7. The guidewire of claim 1, wherein the proximal end portion comprises a hollow tube containing a wire core.

8. The guidewire of claim 7, wherein the wire core extends beyond the proximal end portion to form the central core of the distal end and intermediate portions.

9. The guidewire of claim 1, wherein the proximal end portion has a uniform outside diameter up to the coil and the coil has an outside diameter no less than the uniform outside diameter of the proximal end portion.

10. The guidewire of claim 1, wherein the coil has a proximal end fixed to a distal end of the proximal end portion and a distal end fixed to the end member.

11. The guidewire of claim 1, wherein the first stiffness is sufficient to facilitate guiding of a substantially rigid catheter sheath of a diameter in the range 5 to 7 mm into a bladder via the supra-pubic region of the human body, the second stiffness is less than a stiffness that would cause damage to the wall of the bladder when urged into engagement with the wall, and the stiffness of the intermediate portion is sufficient to provide tactile feedback when the intermediate portion is inserted through a hollow needle to a point proximate the wall of the bladder opposite a point of entry of the guidewire into the bladder.

12. A bladder drainage kit comprising the guidewire of claim 1, a hollow needle having an inside diameter adapted for receiving the guidewire, and a catheter sheath having an internal diameter adapted to receive the guidewire and to penetrate the supra-pubic region of the human body using the proximal end portion of the guidewire as a guide, the catheter sheath having a peelable outer skin.

13. The bladder drainage kit of claim 12, wherein the guidewire has an outside diameter less than 2 mm, and the catheter sheath has an inside diameter at its proximal end of at least 4 mm for receiving a flexible drainage catheter.

14. The bladder drainage kit of claim 12, wherein the catheter sheath further includes an inner sheath for stiffening the peelable outer skin during insertion into the human body, the inner sheath being withdrawable from a proximal end of the peelable outer skin.

15. The bladder drainage kit of claim 14, wherein the inner sheath has a tapered outer surface at its distal end.

16. A method for introducing a catheter into the bladder of the human body in the supra-pubic region comprising the steps of:
   introducing a needle into the bladder via the supra-pubic region;
   inserting the guidewire of claim 1 into the bladder through an internal bore of the needle;
   withdrawing the needle over the guidewire;
   introducing a peelable catheter sheath into the bladder over the guidewire, the catheter sheath having a distal end of outside diameter less than approximately 2 mm and a proximal end having an outside diameter of at least 4 mm;
   withdrawing the guidewire through the catheter sheath;
   inserting a flexible catheter into the bladder through the catheter sheath; and
   peeling away the catheter sheath from the flexible catheter leaving the flexible catheter in situ.

17. A guidewire for introduction into the supra-pubic region of a human body via a hollow needle, comprising a proximal end portion, a distal end portion and an intermediate portion extending between the proximal and distal end portions, the distal end portion and intermediate portion including a central core and a coil surrounding the central core, the proximal end portion having a uniform outside diameter extending up to the coil, the coil having an outside diameter no less than the uniform outside diameter of the proximal end portion adjacent the coil, the central core terminating at and joined to an end member located at a distal end of the coil, and wherein the proximal end portion has a first stiffness, the distal end portion has a second stiffness less than the first stiffness, and the intermediate portion has a stiffness lying between the first stiffness of the proximal end portion and the second stiffness of the distal end portion.

18. The guidewire of claim 17, wherein the coil has a proximal end fixed to a distal end of the proximal end portion and a distal end fixed to the end member.

* * * * *